United States Patent
Dosramos et al.

(10) Patent No.: US 6,604,408 B2
(45) Date of Patent: Aug. 12, 2003

(54) DEVICE FOR USE IN DETERMINING CHARACTERISTICS OF PARTICLES DISPERSED IN A MEDIUM, AND METHOD THEREFOR

(75) Inventors: J. Gabriel Dosramos, Hopedale, MA (US); Robert W. Reed, Stroudsburg, PA (US); Tonis Oja, Scarsdale, NY (US); Gary Boulet, Rindge, NH (US)

(73) Assignee: Matec Instrument Companies, Inc., Northborough, MA (US)

( * ) Notice: Subject to any disclaimer, the term of this patent is extended or adjusted under 35 U.S.C. 154(b) by 0 days.

(21) Appl. No.: 09/798,395

(22) Filed: Mar. 2, 2001

(65) Prior Publication Data

US 2002/0121130 A1 Sep. 5, 2002

(51) Int. Cl.$^7$ ................................................ G01N 29/00
(52) U.S. Cl. .................................... 73/61.75; 73/579
(58) Field of Search ........................... 73/61.71, 61.75, 73/61.79, 61.42, 865.5, 590, 655, 656, 657; 356/37; 702/26

(56) References Cited

U.S. PATENT DOCUMENTS

| | | | | |
|---|---|---|---|---|
| 3,791,200 A | * | 2/1974 | Hayre ........................... 73/574 |
| 4,130,018 A | * | 12/1978 | Adams et al. ............... 310/327 |
| 4,397,183 A | * | 8/1983 | Ballou et al. ............... 250/577 |
| 4,706,509 A | | 11/1987 | Riebel ........................ 73/865.5 |
| 4,763,513 A | * | 8/1988 | Zacharias .................... 310/327 |
| 5,054,319 A | * | 10/1991 | Fling .......................... 250/577 |
| 5,121,629 A | | 6/1992 | Alba .......................... 73/61.41 |
| 5,240,488 A | | 8/1993 | Chandross et al. ........... 65/3.11 |
| 5,291,031 A | * | 3/1994 | MacDonald et al. ......... 250/577 |
| 5,408,874 A | * | 4/1995 | Fleck et al. .................. 367/908 |
| 5,569,844 A | | 10/1996 | Sowerby ..................... 73/61.75 |
| 5,604,301 A | * | 2/1997 | Mountford et al. ......... 73/54.31 |
| 5,739,432 A | * | 4/1998 | Sinha ........................... 73/579 |
| 5,853,994 A | * | 12/1998 | Gopinathan et al. ............ 435/6 |
| 5,952,560 A | * | 9/1999 | Collings et al. ............... 73/599 |
| 6,119,510 A | | 9/2000 | Carasso et al. ............. 73/61.75 |
| 6,324,901 B1 | * | 12/2001 | Fluh et al. ..................... 73/598 |

FOREIGN PATENT DOCUMENTS

FR       2656688 A1  *  7/1991  ............... 73/290 R

* cited by examiner

Primary Examiner—Edward Lefkowitz
Assistant Examiner—Michael Cygan
(74) Attorney, Agent, or Firm—George W. Neuner; Edwards & Angell, LLP (57) ABSTRACT

A device for use in determining the characteristics of particles dispersed in a medium is described. The device has a sample cell for holding a sample containing particles dispersed in a medium. A transducer is positioned to emit sound waves into the sample of the sample cell. A mirror surface is positioned for translational movement within the sample cell without changing the level of the sample in the cell, for movement without the use of dynamic o-ring seals, and is positioned to reflect sound waves emitted by the transducer.

12 Claims, 7 Drawing Sheets

DEVICE FOR USE IN DETERMINING CHARACTERISTICS OF PARTICLES DISPERSED IN A MEDIUM, AND METHOD THEREFOR

FIELD OF THE INVENTION

The present invention related to methods and devices for use in determining the characteristics of particles dispersed in a medium, particularly to such devices that operate with reduced wear and maintenance issues, and which avoid changes in sample level during operation.

BACKGROUND OF THE INVENTION

It often is desirable to know the specific properties of particles dispersed in a liquid medium. For example, larger particles in chemical-mechanical planarization (CMP) often lead to scratches and variations in the median particle size and the size distribution sometimes lead to inconsistent polishing. Similarly, the properties of sol-gel derived bodies depend in large part on the characteristics of the particles in the dispersion. For these reasons, among others, various methods have been developed to determine the characteristics of particles in such dispersions.

One such characteristic is the particle size distribution (PSD). See, for example, U.S. Pat. Nos. 4,706,509, 5,121,629, and 5,569,844. U.S. Pat. No. 4,706,509 describes a method for ultrasonically measuring solids concentration and particle size distribution in a dispersion. Ultrasonic waves at a variety of frequencies are directed into the dispersion, and the attenuation at these frequencies is measured. A dimensional spectrum (across the range of particle dimensions) is divided into dimensional intervals, and a system of linear equations is developed to represent the concentration of particles in each dimension interval. The system of equations is then solved to determine the PSD.

The process described in U.S. Pat. No. 5,569,844 involves measuring the attenuation of both ultrasonic waves and electromagnetic radiation to determine particle size distribution. Specifically, ultrasonic velocity and ultrasonic attenuation are combined with the density, as determined from the electromagnetic radiation attenuation, to calculate the PSD. In addition to the problems inherent in generating x-rays or gamma rays, however, particle sizes of about 10 to 15 μm appear to be the lower limit for the process.

In U.S. Pat. No. 5,121,629, ultrasonic waves at a variety of selected frequencies are passed through a dispersion, and the attenuation at each frequency is measured to derive a measured attenuation spectrum over those frequencies. Separately, based on a theoretical model, a set of attenuation spectra are calculated for a variety of PSDs, and the calculated spectra are then compared to the measured spectrum to formulate a preliminary approximation of the PSD of the dispersion. Further calculations must be performed, starting from this approximation, to more accurately determine the PSD.

U.S. Pat.No. 6,119,510 describes an improved process for determining the characteristics of dispersed particles. The term particles is used to include solids, liquids, or gases dispersed in a continuous medium. Waves (acoustic or light) are directed into a dispersion, and the attenuation of the waves for particular frequencies is measured to provide an attenuation spectrum. The measured attenuation spectrum is then compared to a set of theory-based calculated attenuation spectra to determine the particle size distribution corresponding to the measured attenuation spectrum. Unlike previous processes, the particle size distribution is capable of being accurately determined by a single inversion algorithm. Inversion techniques involve taking a set of known particle size distributions, determining the attenuation spectrum that each PSD would theoretically produce, and comparing a set of such theory-based spectra to the actual, measured spectrum to find the actual PSD.

Acoustic attenuation techniques for characterizing particles in dispersions involve the interaction of applied sound waves with the dispersed particles. As a sound wave travels through a dispersion, the wave loses acoustic energy by various scattering mechanisms. Measurement of the attenuation at different frequencies of the sound wave leads to an acoustic attenuation spectrum. Models by Epstein and Carhart, and by Allegra and Hawley make it possible to predict the attenuation spectrum for particles of a given size distribution and concentration. The models require knowledge of several physical properties of the particles and the liquid medium, including density, thermal expansion coefficient, thermal conductivity, heat capacity, viscosity, and shear rigidity. It is then possible to construct a 3-D matrix that relates attenuation, frequency, and particle size.

Figure 7:
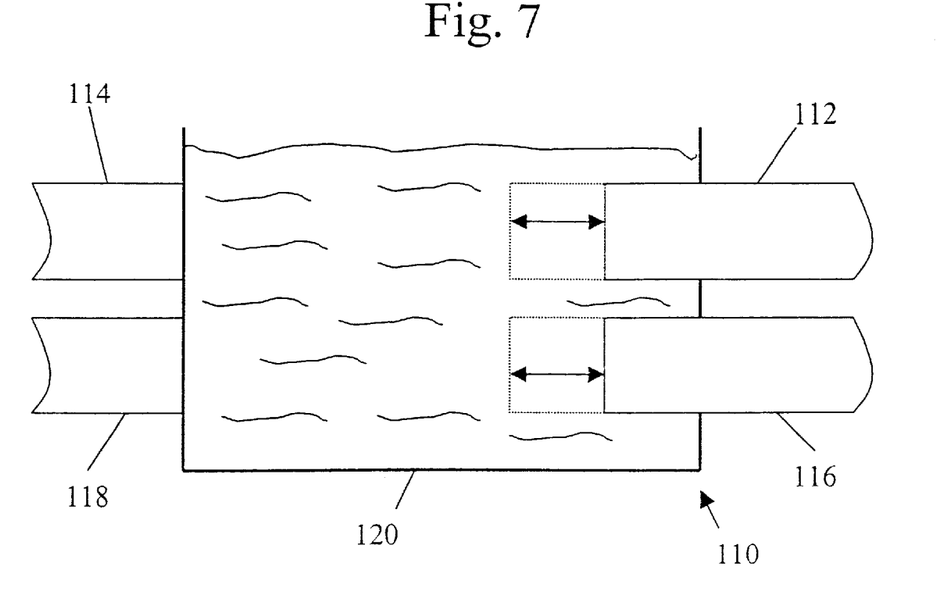
FIG. 7 is a schematic illustration of a prior art apparatus for determination of particle size distribution.

Acoustic attenuation in a particle dispersion can be measured by use of an apparatus such as the Ultrasizer TM, made by Malvern Instruments, Ltd., Worcestershire, United Kingdom (the assignee of U.S. Pat. No. 5,121,629, discussed above). A schematic of the chamber 110 of such an apparatus is shown in FIG. 7. Two pairs of broadband transducers 112, 114, 116, 118, are in contact with a sample located in a tank 120, typically formed of stainless steel. The chamber 110 typically contains a temperature sensor, heater, and a propeller (not shown). It is possible to remove the sample by use of a drain valve at the base of the tank 120. Typically, one pair of transducers 112, 114 covers a lower frequency range, e.g., 1 to 20 MHz, and the other pair 116, 118 a higher range, e.g., 15 to 200 MHz. Generally, the transmitting transducers 112, 116 are capable of being moved to different positions in the chamber, but the receiving transducers 114, 118 are fixed. The spacing between the transmitting transducers 112, 116 and the receiving transducers 114, 118 is controlled by a stepper motor. The transmitting transducers 112, 116 direct a series of planar sound waves, generally at preselected frequencies, across the sample and the receiving transducers detect the attenuated waves. Computer and signal processing equipment is used to control the process of attaining the attenuation spectrum, monitor the detected sound waves, and manipulate the signals generated.

Problems with the prior art devices, such as the apparatus described above, include wear of the seal due to the translation movement of the receiving transducers. That wear causes misalignment of the receiving transducer with the emitting transducer causing major degradation of results due to minute levels of misalignment. The transducers move up to about four inches and, thus, considerable wobble can be experienced due to movement on the o-ring seal. The wear of the seals also can result in leaking of the sample, which can result in a change of the volume sample, i.e., the level of the sample in the sample cell changes. Further, the in/out movement of the variable position transducers in the sample cell causes significant changes in the sample level in the cell. The change in the volume/level of the sample can result in the introduction of sound waves reflected from the liquid surface or a change in the reflection pattern, thereby further degrading the results. Besides sample loss, leaks also can cause electrical damage to the device and sample change. For example, the percent of solids in the sample can change if the medium is leaked preferably to the particles. Also, the shear applied on samples by friction between a moving transducer and an o-ring can cause the particles to aggregate (to form clusters). This particle aggregation can shift the measured particle size to a larger value, thereby rendering the data inaccurate.

Moreover, the semiconductor polishing industry is keen to detect relatively few large particles in the presence of a bulk of small polishing particles. These larger undesirable particles can cause micro-scratches on silicon wafers that result in large financial losses. A particle size measuring instrument that promotes particle aggregation during the measurement can be detrimental to this industry.

Constant wear and tear of the o-ring seal and transducer causes progressive loss of alignment that leads to progressive degradation of data. Thus, frequent replacement of the o-ring seals is required along with tedious alignment of the transducers after each replacement.

Although current apparatus for characterizing dispersed particles, e.g., determining PSD, are adequate, improvements that reduce maintenance and provide more accurate, consistent, and reliable results are desired.

SUMMARY OF THE INVENTION

The present invention provides a new device for use in determining the characteristics of particles dispersed in a medium. The device comprises a sample cell for holding a sample containing particles dispersed in a medium. A stationary transducer is positioned to emit sound waves into the sample through a wall of the sample cell. A mirror surface is positioned for translational movement in the sample cell without the need for dynamic o-rings and without changing the level of the sample in the cell and is positioned to reflect sound waves emitted by the transducer.

In a preferred embodiment, a device in accord with the present invention comprises a support plate, a sample cell having at least one side wall, the sample cell being mounted on the support plate, a transducer having a first end positioned in said side wall and a second end in an alignment ring that is mounted on said support plate, a mirror surface positioned in the sample cell, a high-precision translation stage for moving the mirror surface linearly within the sample cell, the translation stage being attached to said support plate, the mirror surface being mounted on the translation stage and being positioned in the sample cell without movement through a wall of the sample cell.

The present invention also provides a method for determining the characteristics of particles dispersed in a medium. The method comprises providing a device as described hereinabove, providing a sample having particles dispersed in a medium for determining the characteristics of the particles, and using the device to obtain attenuation of sound waves for particular frequencies to provide an attenuation spectrum.

A particularly useful advantage of the present invention is the elimination of dynamic o-ring seals of the prior art devices having variable position transducers.

DETAILED DESCRIPTION OF THE INVENTION INCLUDING PREFERRED EMBODIMENTS THEREOF

The present invention provides a device used for determining the characteristics of particles dispersed in a medium. A process for determining the characteristics of the particles involves directing acoustic waves into a dispersion of the particles and measuring the attenuation of the sound waves for particular frequencies to provide an attenuation spectrum. An inversion technique is performed to determine the particle size distribution corresponding to the measured attenuation spectrum. The measured attenuation spectrum is compared to a set of theory-based calculated attenuation spectra. A preliminary approximation of the particle size distribution is not required. See, for example, U.S. Pat. No. 6,119,510, the disclosure of which is hereby incorporated by reference.

Figure 1:
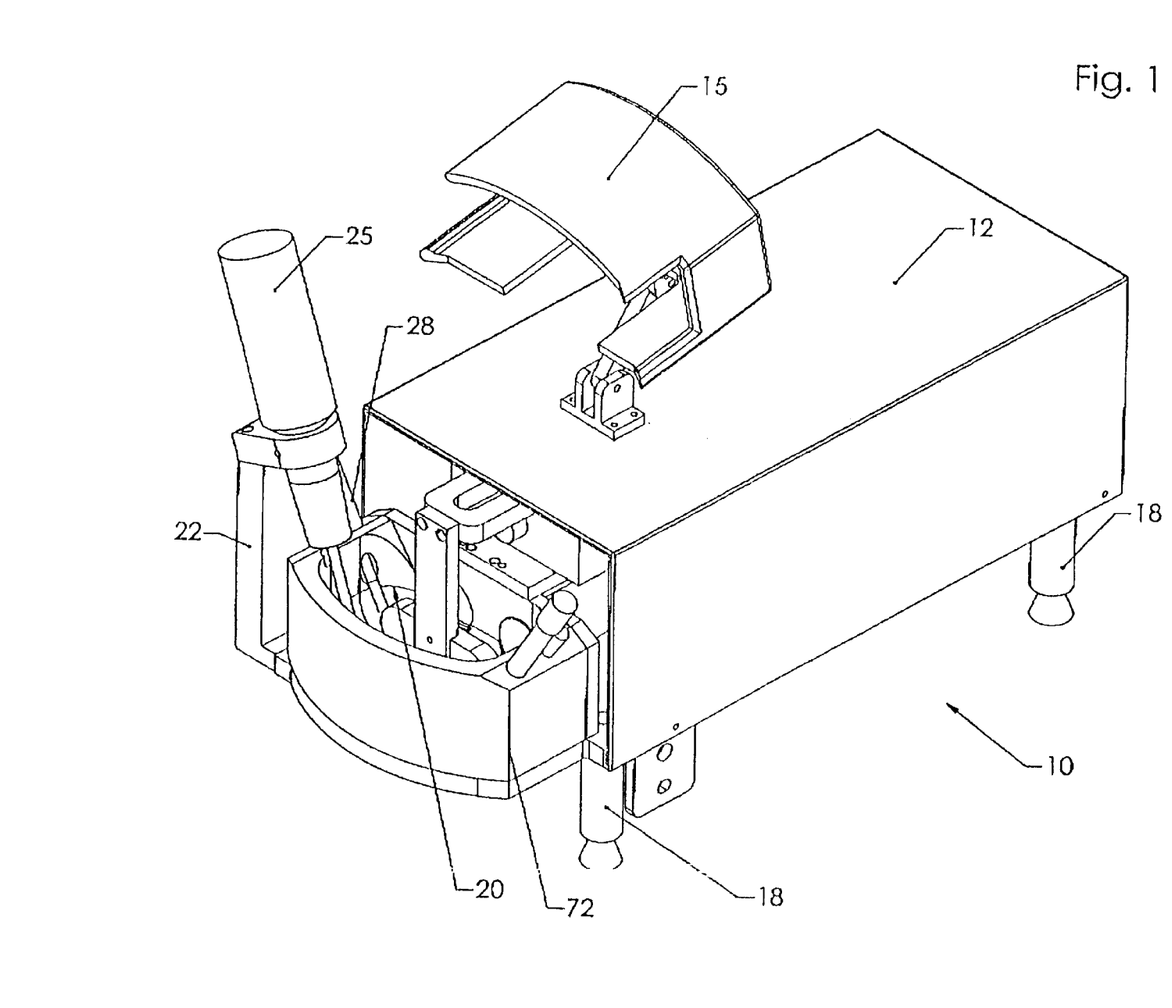
FIG. 1 is an isometric view of a device for determining the characteristics of particles dispersed in a medium in accord with one embodiment of the present invention.

With reference to the drawings, a device in accord with one embodiment of the present invention is illustrated. As illustrated in FIG. 1, the device 10 has a housing with a movable cover 15 for enclosing the sample well 20 during operation. A mounting bracket 22 can be used to hold additional devices that may be used during operation such as, for example, a mixer 25 and a temperature probe 28, among others. Adjustable legs 18 (two shown) are provided for leveling the device.

Figure 2:
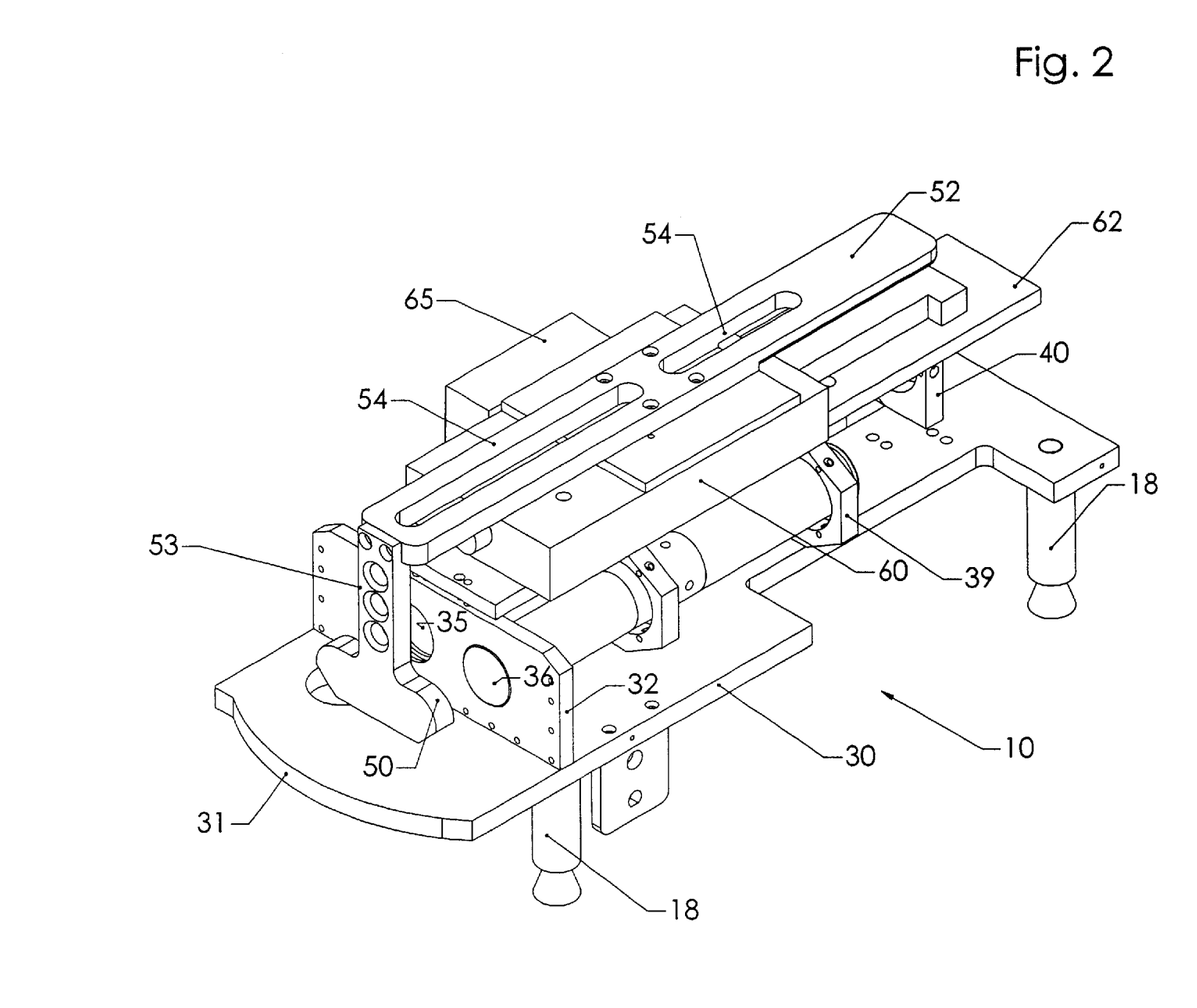
FIG. 2 is an isometric view of a partial device for determining the characteristics of particles dispersed in a medium in accord with one embodiment of the present invention.

As illustrated in FIG. 2, the device 10 has a main support plate 30 that is supported by the legs 18 and on which other components of the device are mounted. A vertical end wall 32 is mounted on the support plate and positioned near one end of the device where the sample well will be located. The vertical end wall 32 conveniently forms one side of the sample well (see FIG. 3). The end wall preferably is made from a material that will minimize alignment loss due to deformation (e.g., stainless steel instead of a plastic). Openings 35, 36 are provided in the end wall to sealingly hold the ends of two transducers. One transducer 37 is shown. The second transducer (not shown) is located behind transducer 37. One of the transducers emits sound waves having a frequency in the range of from about 1 to about 25 MHz. The second transducer emits sound waves having a higher frequency in the range of from about 10 to about 100 MHz. The opposite end of each transducer is held in an alignment ring 39, 40 that is used to align the transducers for optimal performance. One end of the second transducer is mounted in opening 35 and the other end is supported in alignment ring 40. The alignment rings 39, 40 are mounted on support plate 30. Each ring has three extremely fine alignment screws (e.g., 80 pitch thread; not shown) spaced 120 degrees apart.

The device also has a mirror plate 50 having a polished mirror surface facing the ends of the transducers in the openings 35, 36. The mirror plate 50 is supported from a counterbalanced arm 52 by extension arm 53. The counterbalanced arm has openings 54 to reduce weight while providing stability. A translation stage 60 permits the mirror plate 50 to travel linearly to vary the distance between the transducers and the polished mirror surface. The translation stage preferably should permit positioning to an accuracy of 1 µm with a repeatability within 0.2 µm while maintaining pitch and yaw each within 50 µrad for a travel distance of from about 0.05 to about 2.0 inch. suitable translation stages include the M-400 series, particularly model M-405 DG, which can be obtained from Physik Instrumente GmbH & Co., Waldbrom, Germany. The translation stage is mounted on a translation support plate 62, which is mounted to the end wall 32 and alignment rings 39, 40. A transducer output signal pre-amplifier 65 also is mounted (not shown) to the main support plate 30.

Figure 3:
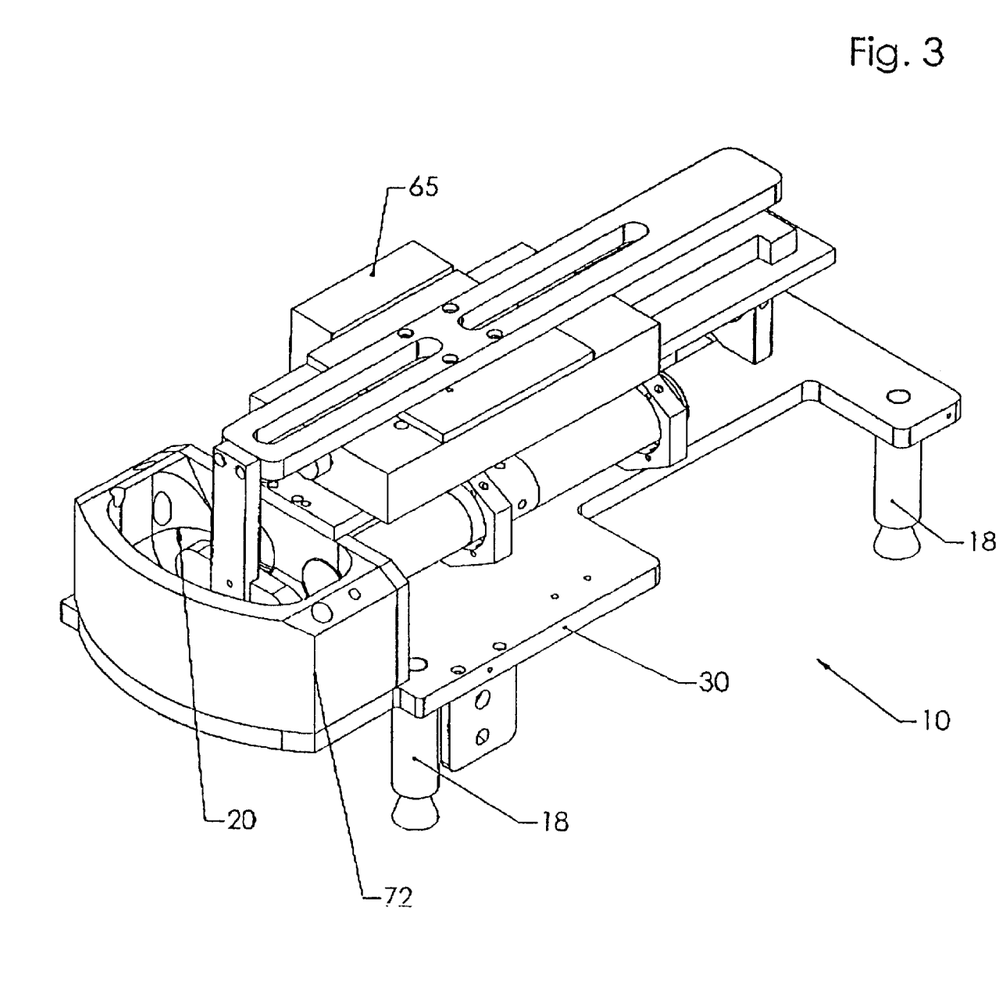
FIG. 3 is an isometric view of the device of FIG. 2 further illustrating a sample cell.
Figure 4:
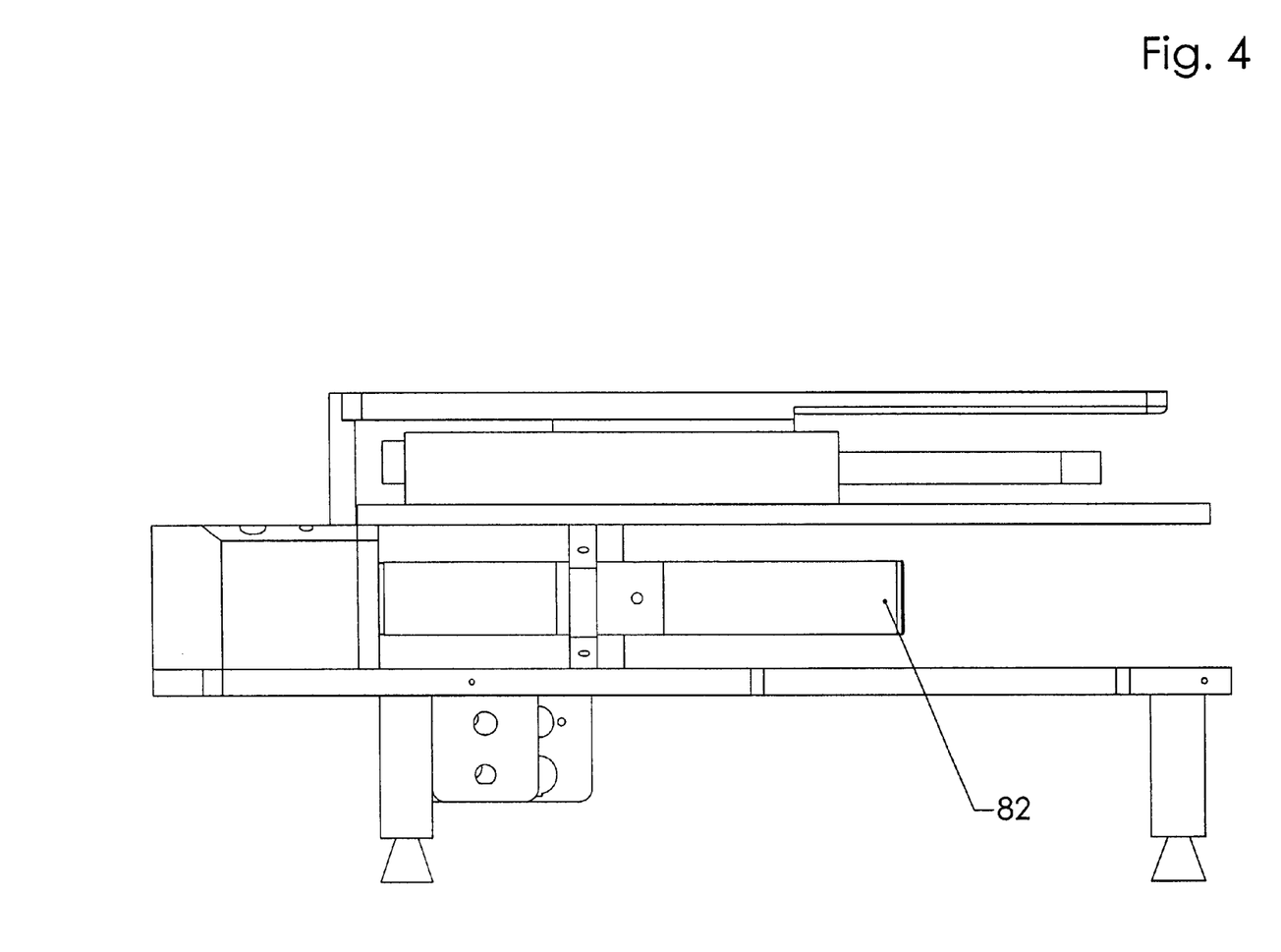
FIG. 4 is a side view of the device of FIG. 3.

The sample well 20 is formed by sealingly attaching an end piece 72 to the end 31 of the main support plate 30 and the end wall 32. Openings are provided to accommodate various optional devices that may be used in connection with the measurements performed by the device 10.

Figure 5:
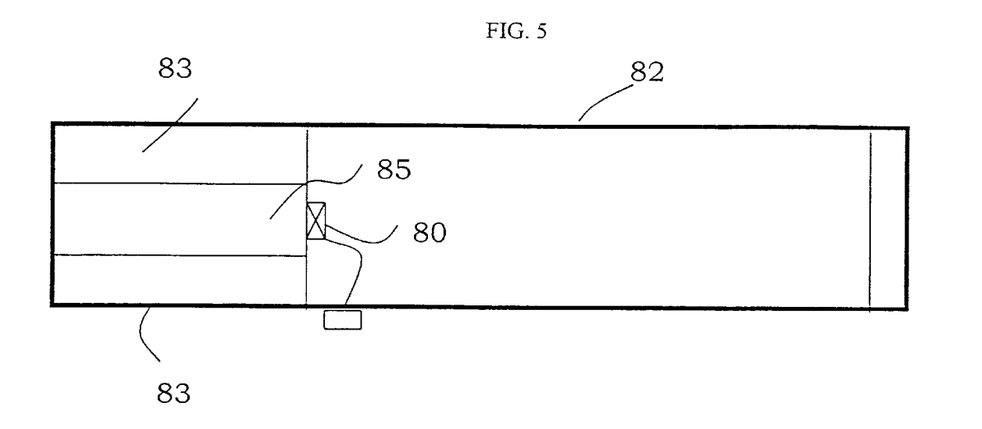
FIG. 5 is a schematic side view of a transducer assembly for use in connection with the present invention.
Figure 6:
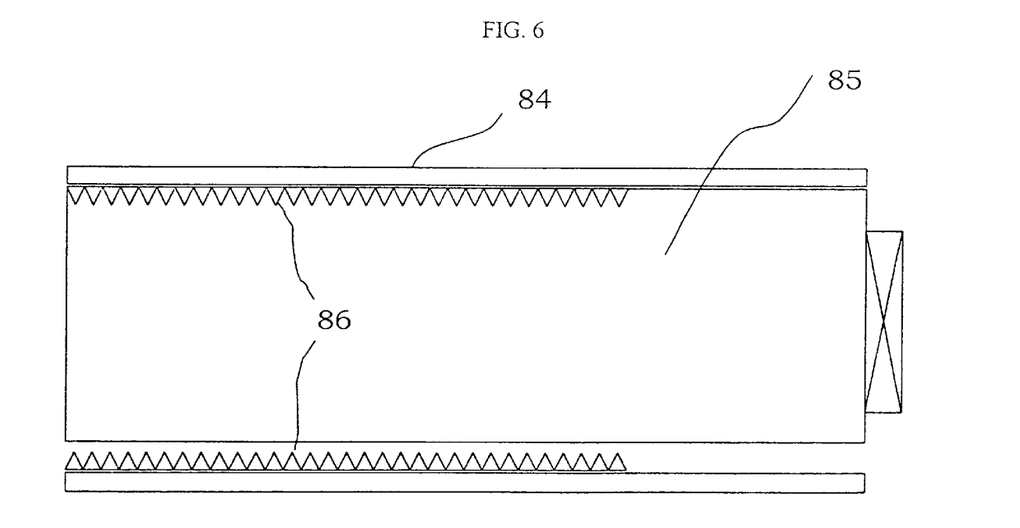
FIG. 6 is a schematic side view of a quartz delay rod for use in the transducer assembly of FIG. 5.

As illustrated in FIG. 5, each transducer 80 is housed in a continuous tube 82 having sufficient length to house the transducer and accommodate desired alignment accuracy. Typically, a length of about 15 inches is satisfactory for the tube. A quartz rod 85 preferably is positioned between the transducer and the sample to delay the sound waves. The delay facilitates using the transducer for both an emitter and a receiver. A 19.5 µsec delay was found satisfactory in the present embodiment. The quartz rod preferably has grooves 86 to reduce undesirable sound echoes (noise) (see FIG. 6). These echoes can overlap with and, thus, distort the desirable attenuated sound waves. Grooves having a depth of 0.035 inch are suitable. The quartz rod 85 is held by epoxy 84 in a resin sleeve 83 inside the tube 82. A Delrin® material is suitable for the resin sleeve 85. A tungsten-loaded epoxy is suitable for dampening the undesirable sound echoes. The tube 82 preferably is a stainless steel tube. Other suitable materials are readily substituted by those skilled in the art.

The structural elements of the device 10 can be made from any suitable material. Aluminum was used for the support plates 30, 62 in the described embodiment to reduce weight. The end wall 32 was made of stainless steel for stiffness. The mirror plate 50 and its supporting structure including counterbalance arm 52 and extension arm 53 were made of stainless steel. The end piece 72 for completing the sample well 70 was made of Teflon®. Other suitable materials are readily substituted by those skilled in the art.

With a device in accord with the present invention, there are no seals required for a moving transducer. Thus, there is no degradation of performance do to seal wear and misalignment caused thereby. There is no wear on the seals or the transducers in a device according to the present invention. Also, the liquid level remains constant and sound is not reflected off the liquid surface in a varying manner during sample testing. This liquid surface reflected sound can overlap with, and thereby distort, the desired attenuated sound wave. The present invention eliminates the need to replace seals for a moving transducer and the necessary alignment of transducers after such replacement. Devices in accord with the present invention are capable of providing more consistent long term accuracy and reproducibility of results with lower maintenance than prior art devices.

Very fine alignment is required whether an emitter/receiver transducer pair or an emitter/reflector pair setup is used. In fact, the prior art emitter/receiver setup requires that both transducers be aligned relative to each other thereby making the alignment process more tedious and time consuming. In the proposed invention, only the transducer need be aligned against a perpendicular reflector.

Figure 8:
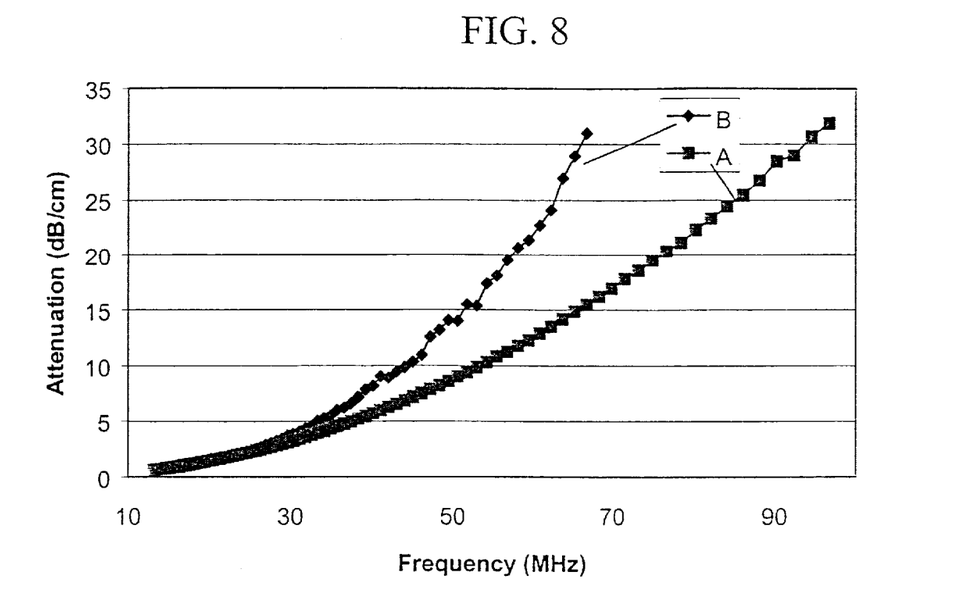
FIG. 8 is a graph illustrating the relationship of attenuation of sound waves with the frequency for aligned transducer (A) and misaligned transducer (B).
Figure 9:
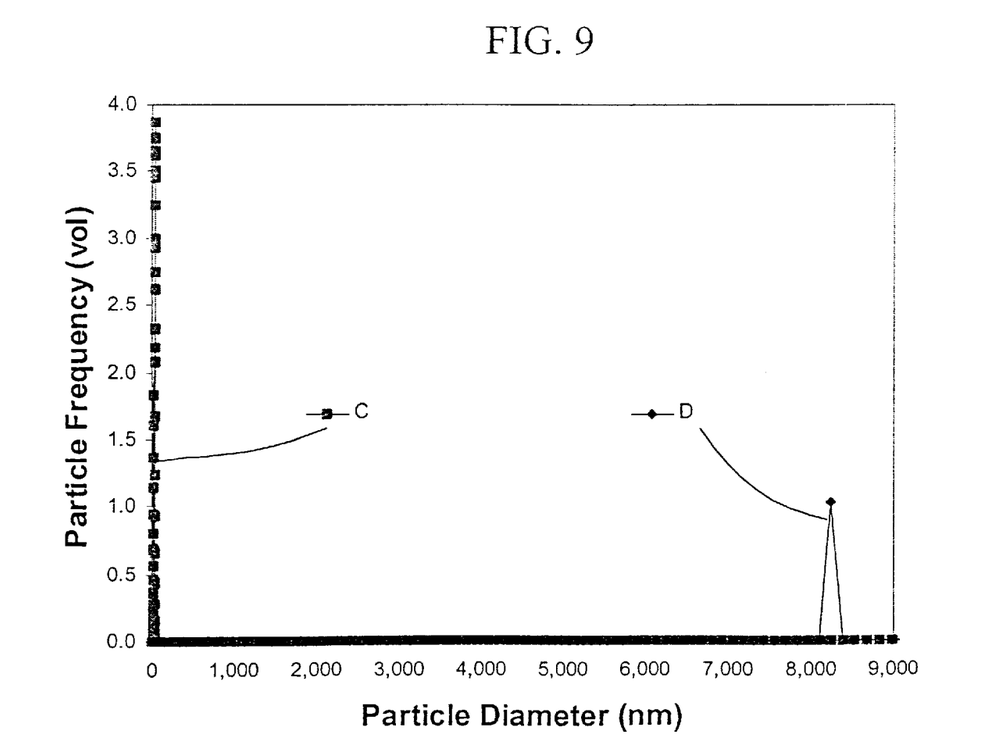
FIG. 9 is a graph illustrating the effect of misalignment on calculated particle size where curve C is the particle size for an aligned transducer and curve D is the particle size for a misaligned transducer.

FIGS. 8 and 9 illustrate the need for extremely fine alignment, thereby showing the significant advantage of not using dynamic O-rings. FIG. 8 contains two acoustic attenuation spectra curves, dB/cm vs. frequency in MHz, for a Ludox TM colloidal silica manufactured by DuPont, Wilmington, Del. This silica has been characterized by numerous techniques to have a mean particle size in the range 25 to 35 nm. Curve A was obtained with a finely aligned transducer/reflector system; curve B was obtained after purposely turning an alignment-ring screw ⅟₆₄" which corresponds to a misalignment of only 0.09 degrees (considering that in the present embodiment, the alignment ring is located 9 inches from the transducer end).

As typically required by the acoustic-attenuation particle size measurement process, data was collected at eight different reflector/transducer spacings (cm) as follows: 0.3497, 0.4997, 0.7997, 1.1997, 1.9998, 2.6997, 3.4997, and 4.1997. Please note that an emitter/receiver transducer pair would require that these spacings be doubled because sound travels only once through these paths. Attenuation must be measured at multiple spacings for two reasons as follows: (i) high frequency measurements must be made at narrow paths while the opposite happens at low frequencies; and (ii) the attenuation curve must be built with as many as 100 data points in order to produce reliable particle size distribution data.

Curve B (data using misaligned transducer) in FIG. 8 is jagged and shifted noticeably from curve A. The detrimental effect on the resulting particle size distribution (PSD) data is shown in FIG. 9. This data was calculated using the methods described in U.S. Pat. No. 6,119,510. Curve C is the PSD curve for the aligned transducer. Curve D corresponds to the slightly misaligned (0.09 degrees) transducer. The effect on the calculated particle size is catastrophic. Curve C shows a mean particle size of about 32 nm. Curve D produces a mean particle size of about 8,240 nm, an error of about 25,650%. Also, the Y-axis calculated absolute particle concentration (frequency) in FIG. 9 is significantly larger for curve C (3.9%) than D (1%)

The invention has been described in detail including preferred embodiments thereof. However, it will be appreciated that those skilled in the art may make modifications and improvements within the spirit and scope of this invention.

What is claimed is:

1. A device for use in determining the characteristics of particles dispersed in a medium, the device comprising:
    a sample cell for holding a sample containing particles dispersed in a medium and having a wall;
    a stationary transducer positioned in the wall to emit sound waves into the sample;
    a mirror surface positioned in the sample cell to reflect sound waves emitted by the transducer; and
    means for for translational movement of the mirror surface in the sample cell without passing through an opening in a wall of the sample cell and without changing a fluid level of the sample in the cell.

2. The device of claim 1, wherein the transducer is both an emitter and a receiver.

3. The device of claim 2, wherein the transducer includes a delay.

4. The device of claim 3, wherein the delay is implemented using a quartz rod.

5. A device for use in determining the characteristics of particles dispersed in a medium, the device comprising:
- a sample cell for holding a sample containing particles dispersed in a medium and having a wall;
- a stationary transducer positioned in the wall to emit sound waves into the sample;
- a mirror surface positioned in the sample cell to reflect sound waves emitted by the transducer; and
- means for for translational movement of the mirror surface in the sample cell without passing through an opening in a wall of the sample cell and without changing a fluid level of the sample in the cell;
- wherein the transducer is both an emitter and a receiver;
- wherein the transducer includes a delay;
- wherein the delay is implemented using a quartz rod; and
- wherein the quartz rod has grooves on its surface.

6. A device comprising:
- a support plate;
- a sample cell having at least one side wall, the sample cell being mounted on the support plate;
- an alignment ring mounted on said support plate;
- a transducer having a first end positioned in said side wall and a second end in said alignment ring;
- a mirror surface positioned in the sample cell;
- a translation stage for moving the mirror surface linearly within the sample cell, the translation stage being attached to said support plate, the mirror surface being mounted on the translation stage and being positioned in the sample cell without movement of a supporting structure for the mirror surface through a wall of the sample cell.

7. The device of claim 6, wherein the transducer is both an emitter and a receiver.

8. The device of claim 7, wherein the transducer includes a delay.

9. The device of claim 8, wherein the delay is implemented using a quartz rod.

10. A device comprising:
- a support plate;
- a sample cell having at least one side wall, the sample cell being mounted on the support plate;
- an alignment ring mounted on said support plate;
- a transducer having a first end positioned in said side wall and a second end in said alignment ring;
- a mirror surface positioned in the sample cell;
- a translation stage for moving the mirror surface linearly within the sample cell, the translation stage being attached to said support plate, the mirror surface being mounted on the translation stage and being positioned in the sample cell without movement of a supporting structure for the mirror surface through a wall of the sample cell;
- wherein the transducer is both an emitter and a receiver;
- wherein the transducer includes a delay;
- wherein the delay is implemented using a quartz rod; and
- wherein the quartz rod has grooves on its surface.

11. A method for determining the characteristics of particles dispersed in a medium, the method comprising:
- providing a device having:
  - a sample cell for holding a sample containing particles dispersed in a medium and having a wall;
  - a transducer positioned in the wall to emit sound waves into the sample; and
  - a mirror surface positioned for translational movement in the sample cell without passing through an opening in a wall of the sample cell, without changing a fluid level of the sample in the cell and positioned to reflect sound waves emitted by the transducer;
- providing a sample having particles dispersed in a medium for determining the characteristics of the particles; and
- using the device to obtain attenuation of sound waves for particular frequencies to provide an attenuation spectrum.

12. A method for determining the characteristics of particles dispersed in a medium, the method comprising:
- providing a device comprising:
  - a support plate;
  - a sample cell having at least one side wall, the sample cell being mounted on the support plate;
  - an alignment ring mounted on said support plate;
  - a transducer having a first end positioned in said side wall and a second end in said alignment ring;
  - a mirror surface positioned in the sample cell;
  - a translation stage for moving the mirror surface linearly within the sample cell, the translation stage being attached to said support plate, the mirror surface being mounted on the translation stage and being positioned in the sample cell without movement through a wall of the sample cell;
- providing a sample having particles dispersed in a medium for determining the characteristics of the particles; and
- using the device to obtain attenuation of sound waves for particular frequencies to provide an attenuation spectrum.

* * * * *